US010123896B2

(12) United States Patent
Farrugia et al.

(10) Patent No.: US 10,123,896 B2
(45) Date of Patent: Nov. 13, 2018

(54) APPARATUS AND METHODS OF INDUCING WEIGHT LOSS USING BLOOD FLOW CONTROL

(71) Applicant: Mayo Foundation for Medical Education and Research, Rochester, MN (US)

(72) Inventors: Gianrico Farrugia, Rochester, MN (US); Paul A. Friedman, Rochester, MN (US); Elizabeth Rajan, Rochester, MN (US); Charles J. Bruce, South Ponte Vedra Beach, FL (US); Samuel J. Asirvatham, Rochester, MN (US); Michael J. Levy, Rohester, MN (US); Louis-Michel Wong Kee Song, Rochester, MN (US); Juliane Bingener-Casey, Rochester, MN (US); Navtej S. Buttar, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/123,094

(22) PCT Filed: Mar. 5, 2015

(86) PCT No.: PCT/US2015/018965
§ 371 (c)(1),
(2) Date: Sep. 1, 2016

(87) PCT Pub. No.: WO2015/134747
PCT Pub. Date: Sep. 11, 2015

(65) Prior Publication Data
US 2017/0105860 A1    Apr. 20, 2017

Related U.S. Application Data

(60) Provisional application No. 61/949,024, filed on Mar. 6, 2014.

(51) Int. Cl.
| | | |
|---|---|---|
| *A61F 5/00* | (2006.01) | |
| *A61F 7/12* | (2006.01) | |
| *A61N 1/36* | (2006.01) | |
| *A61N 1/05* | (2006.01) | |
| *A61B 5/03* | (2006.01) | |
| *A61B 5/00* | (2006.01) | |
| *A61B 5/026* | (2006.01) | |
| *A61B 17/12* | (2006.01) | |
| *A61B 18/14* | (2006.01) | |
| *A61B 18/18* | (2006.01) | |
| *A61B 18/00* | (2006.01) | |
| *A61B 17/00* | (2006.01) | |

(52) U.S. Cl.
CPC ............ *A61F 5/0013* (2013.01); *A61B 5/026* (2013.01); *A61B 5/03* (2013.01); *A61B 5/4205* (2013.01); *A61B 5/4238* (2013.01); *A61B 17/12013* (2013.01); *A61B 18/1492* (2013.01); *A61B 18/1815* (2013.01); *A61F 7/123* (2013.01); *A61N 1/0556* (2013.01); *A61N 1/36007* (2013.01); *A61B 2017/00818* (2013.01); *A61B 2018/00404* (2013.01); *A61B 2018/00577* (2013.01); *A61B 2018/00613* (2013.01); *A61F 2007/126* (2013.01)

(58) Field of Classification Search
CPC .............................. A61F 5/0013; A61F 7/123
See application file for complete search history.

(56) References Cited

U.S. PATENT DOCUMENTS

| | | | |
|---|---|---|---|
| 4,315,509 | A | 2/1982 | Smit |
| 4,501,264 | A | 2/1985 | Rockey |
| 4,592,339 | A | 6/1986 | Kuzmak et al. |
| 4,763,653 | A | 8/1988 | Rockey et al. |
| 5,088,979 | A | 2/1992 | Filipi et al. |
| 5,188,104 | A | 2/1993 | Wernicke et al. |
| 5,199,430 | A | 4/1993 | Fang et al. |
| 5,226,429 | A | 7/1993 | Kuzmak |
| 5,231,988 | A | 8/1993 | Wernicke et al. |
| 5,246,456 | A | 9/1993 | Wilkinson |
| 5,259,847 | A | 11/1993 | Trambert |
| 5,263,480 | A | 11/1993 | Wernicke et al. |
| 5,306,300 | A | 4/1994 | Berry |
| 5,308,326 | A | 5/1994 | Zimmon |
| 5,423,872 | A | 6/1995 | Cigaina |
| 5,514,175 | A | 5/1996 | Kim et al. |
| 5,540,730 | A | 7/1996 | Terry et al. |
| 5,549,621 | A | 8/1996 | Bessler et al. |
| 5,836,994 | A | 11/1998 | Bourgeois |

(Continued)

FOREIGN PATENT DOCUMENTS

| | | |
|---|---|---|
| WO | WO 01/41671 A2 | 6/2001 |
| WO | WO 01/89393 A1 | 11/2001 |

(Continued)

OTHER PUBLICATIONS

U.S. Appl. No. 61/784,915, filed Mar. 14, 2013, Mortarless Technologies LLC.

(Continued)

*Primary Examiner* — Zohreh A Fay
(74) *Attorney, Agent, or Firm* — Mueting, Raasch & Gebhardt, P.A.

(57) ABSTRACT

Methods and apparatus for inducing weight loss using blood flow control are described herein. The apparatus and methods operate by controlling blood flow to the stomach and/or small bowel.

13 Claims, 1 Drawing Sheet

(56) References Cited

U.S. PATENT DOCUMENTS

| | | |
|---|---|---|
| 5,995,872 A | 11/1999 | Bourgeois |
| 6,067,991 A | 5/2000 | Forsell |
| 6,097,984 A | 8/2000 | Douglas |
| 6,104,955 A | 8/2000 | Bourgeois |
| 6,115,635 A | 9/2000 | Bourgeois |
| 6,210,347 B1 | 4/2001 | Forsell |
| 6,216,039 B1 | 4/2001 | Bourgeois |
| 6,243,607 B1 | 6/2001 | Mintchev et al. |
| 6,302,917 B1 | 10/2001 | Dua et al. |
| 6,327,503 B1 | 12/2001 | Familoni |
| 6,341,236 B1 | 1/2002 | Osorio et al. |
| 6,369,079 B1 | 4/2002 | Rubin et al. |
| 6,449,511 B1 | 9/2002 | Mintchev et al. |
| 6,453,907 B1 | 9/2002 | Forsell |
| 6,454,699 B1 | 9/2002 | Forsell |
| 6,460,543 B1 | 10/2002 | Forsell |
| 6,461,293 B1 | 10/2002 | Forsell |
| 6,471,635 B1 | 10/2002 | Forsell |
| 6,475,136 B1 | 11/2002 | Forsell |
| 6,535,764 B2 | 3/2003 | Imran et al. |
| 6,540,789 B1 | 4/2003 | Silverman et al. |
| 6,558,400 B2 | 5/2003 | Deem et al. |
| 6,558,708 B1 | 5/2003 | Lin |
| 6,571,127 B1 | 5/2003 | Ben-Haim et al. |
| 6,572,629 B2 | 6/2003 | Kalloo et al. |
| 6,587,719 B1 | 7/2003 | Barrett et al. |
| 6,600,953 B2 | 7/2003 | Flesler et al. |
| 6,609,025 B2 | 8/2003 | Barrett et al. |
| 6,611,715 B1 | 8/2003 | Boveja |
| 6,615,084 B1 | 9/2003 | Cigaina |
| 6,684,105 B2 | 1/2004 | Cohen et al. |
| 6,736,828 B1 | 5/2004 | Adams et al. |
| 6,746,489 B2 | 6/2004 | Dua et al. |
| 6,754,536 B2 | 6/2004 | Swoyer et al. |
| 6,853,862 B1 | 2/2005 | Marchal et al. |
| 6,928,320 B2 | 8/2005 | King |
| 6,993,391 B2 | 1/2006 | Flesler et al. |
| 7,037,344 B2 | 5/2006 | Kagan et al. |
| 7,803,195 B2 | 9/2010 | Levy et al. |
| 7,998,220 B2 | 8/2011 | Murphy |
| 8,372,158 B2 | 2/2013 | Levy et al. |
| 9,498,366 B2 | 11/2016 | Burnett et al. |
| 2001/0011543 A1 | 8/2001 | Forsell |
| 2001/0037127 A1 | 11/2001 | De Hoyos Garza |
| 2002/0022851 A1 | 2/2002 | Kalloo et al. |
| 2002/0055757 A1 | 5/2002 | Toore et al. |
| 2002/0165589 A1 | 11/2002 | Imran et al. |
| 2002/0183768 A1 | 12/2002 | Deem et al. |
| 2002/0188354 A1 | 12/2002 | Peghini |
| 2003/0018367 A1 | 1/2003 | DiLorenzo |
| 2003/0040804 A1 | 2/2003 | Stack et al. |
| 2003/0040808 A1 | 2/2003 | Stack et al. |
| 2003/0045909 A1 | 3/2003 | Gross et al. |
| 2003/0069533 A1 | 4/2003 | Kakutani et al. |
| 2003/0078611 A1 | 4/2003 | Hashiba et al. |
| 2003/0158601 A1 | 8/2003 | Silverman et al. |
| 2003/0167024 A1 | 9/2003 | Imran et al. |
| 2003/0167025 A1 | 9/2003 | Imran et al. |
| 2003/0171760 A1 | 9/2003 | Gambale |
| 2003/0191476 A1 | 10/2003 | Smit |
| 2003/0199991 A1 | 10/2003 | Stack et al. |
| 2003/0216749 A1 | 11/2003 | Ishikawa et al. |
| 2003/0220660 A1 | 11/2003 | Kortenbach et al. |
| 2004/0015201 A1 | 1/2004 | Greenstein |
| 2004/0019388 A1 | 1/2004 | Starkebaum |
| 2004/0037865 A1 | 2/2004 | Miller |
| 2004/0039427 A1 | 2/2004 | Barrett et al. |
| 2004/0039452 A1 | 2/2004 | Bessler |
| 2004/0044357 A1 | 3/2004 | Gannoe et al. |
| 2004/0059393 A1 | 3/2004 | Policker et al. |
| 2004/0088022 A1 | 5/2004 | Chen |
| 2004/0089313 A1 | 5/2004 | Utley et al. |
| 2004/0092892 A1 | 5/2004 | Kagan et al. |
| 2004/0092974 A1 | 5/2004 | Gannoe et al. |
| 2004/0093091 A1 | 5/2004 | Gannoe et al. |
| 2004/0107004 A1 | 6/2004 | Levine et al. |
| 2004/0138760 A1 | 7/2004 | Schurr et al. |
| 2004/0167583 A1 | 8/2004 | Knudson et al. |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172142 A1 | 9/2004 | Stack et al. |
| 2004/0176812 A1 | 9/2004 | Knudson et al. |
| 2004/0199087 A1 | 10/2004 | Swain et al. |
| 2005/0033331 A1 | 2/2005 | Burnett et al. |
| 2005/0038484 A1 | 2/2005 | Knudson et al. |
| 2005/0055039 A1 | 3/2005 | Burnett et al. |
| 2005/0070970 A1 | 3/2005 | Knudson et al. |
| 2005/0070974 A1 | 3/2005 | Knudson et al. |
| 2005/0177181 A1 | 8/2005 | Kagan et al. |
| 2005/0228504 A1 | 10/2005 | Demarais |
| 2005/0277957 A1 | 12/2005 | Kuhns et al. |
| 2006/0004410 A1 | 1/2006 | Nobis et al. |
| 2006/0015125 A1 | 1/2006 | Swain |
| 2006/0020247 A1 | 1/2006 | Kagan et al. |
| 2006/0036293 A1 | 2/2006 | Whitehurst et al. |
| 2006/0189889 A1 | 8/2006 | Gertner |
| 2007/0265709 A1 | 11/2007 | Rajan et al. |
| 2009/0048624 A1 | 2/2009 | Alverdy |
| 2010/0185220 A1 | 7/2010 | Naghavi et al. |
| 2011/0130701 A1 | 6/2011 | Stergiopulos |
| 2013/0096580 A1 | 4/2013 | Cohn et al. |
| 2013/0184635 A1 | 7/2013 | Levy et al. |

FOREIGN PATENT DOCUMENTS

| | | |
|---|---|---|
| WO | WO 02/087657 A2 | 11/2002 |
| WO | WO 02/089655 A2 | 11/2002 |
| WO | WO 03/094785 A1 | 11/2003 |
| WO | WO 2004/05810 A2 | 7/2004 |
| WO | WO 2004/086984 A1 | 10/2004 |
| WO | WO 2010/005436 A1 | 1/2010 |

OTHER PUBLICATIONS

Bresnick, "Will Google Glass find a home in healthcare?" *HER Intelligence*, Mar. 13, 2013, http://ehrintelligence.com/2013/03/13/will-google-glass-find-a-home-in-healthcare/.

Cennamo et al., "A Rare Gastric Ulcer Complication: the Gastrocolic Fistula. A Case Report," *Chirurgia Italiana*, 2001, 53(6):869-872.

Fazel et al., "Prophylactic Pancreatic Duct Stenting: A Panacea?," *Gastroenterology*, Oct. 2003, 125(4):1274-1275.

Fried, "New iPhone App Lets Users Count Calories Without Burning Any," *AllThingsD*, The Wall Street Journal, Apr. 5, 2011, http://allthingsd.com/20110405/new-iphone-app-lets-users-count-calories-without-burning-any/.

Itoi et al., "Novel EUS-guided gastrojejunostomy technique using a new double-balloon enteric tube and lumen-apposing metal stent," 2013, *Gastrointestinal Endoscopy*, 78(6): 934-939.

International Search Report and Written Opinion dated Jun. 18, 215 for International Application No. PCT/US2015/018965, 14 pgs.

International Preliminary Report on Patentability dated Sep. 15, 2016 for International Application No. PCT/US2015/018965, 9 pgs.

Kilgore et al., "Nerve Conduction Block Utilising High-Frequency Alternating Current," *Medical & Biological Engineering & Computing*, 2004, 42:394-406.

Life on Tech, http://lifeontech.com/2013/06/03/40-google-glass-apps-available-now/.

Pitsinis et al., "Gastrocolic Fistula as a Complication of Percutaneous Endoscopic Gastrostomy," *European Journal of Clinical Nutrition*, 2003 , 57:876-878.

Product Brochure, "ATROSTIM Phrenic Nerve Stimulator," AtroTech Oy, P.O. Box 28, FIN-33721 Tampere, Finland, 2 pages (Jun. 2004).

Pugh, "AR Dieting System Changes Look of Food So Users Eat Less," *PSFK*, Dec. 16, 2012, http://www.psfk.com/2012/12/augmented-reality-dieting.html.

Schauer et al., "Surgical Management of Gastroesophageal Reflux Disease in Obese Patients," *Seminars in Laparoscopic Surgery*, Dec. 2001, 8(4):256-264.

(56) References Cited

OTHER PUBLICATIONS

Sturm et al., "Energy Intake and Appetite are Related to Antral Area in Healthy Young and Older Subjects," *Am. J. Clin. Nutr.*, 2004, 80:656-667.

Tavenor et al., "Gastrocolic Fistula. A Review of 15 Cases and an Update of the Literature," *J. Clin. Gastroenterol.*, 1993, 16(3):189-191.

Thyssen et al., "Medical Treatment of Benign Gastrocolic Fistula," *Annals of Internal Medicine*, Mar. 15, 1993, 118:433-435.

Wagtmans et al., "Persistent Diarrhoea in Cholecystocolic and Gastrocolic Fistula after Gastric Surgery," *Netherlands Journal of Medicine*, Dec. 2013, 43(5-6):218-221.

APPARATUS AND METHODS OF INDUCING WEIGHT LOSS USING BLOOD FLOW CONTROL

RELATED APPLICATION

The present application is the § 371 U.S. National Stage Application of International Application No. PCT/US2015/018965, titled APPARATUS AND METHODS OF INDUCING WEIGHT LOSS USING BLOOD FLOW CONTROL, filed Mar. 5, 2015 which, claims the benefit under 35 U.S.C. § 119(e) of U.S. Provisional Patent Application No. 61/949,024, filed on Mar. 6, 2014 and titled APPARATUS AND METHODS OF INDUCING WEIGHT LOSS USING BLOOD FLOW CONTROL, which are hereby incorporated by reference in their entireties.

Apparatus and methods of inducing weight loss using blood flow control are described herein. The apparatus and methods operate by controlling blood flow to the stomach and/or small bowel.

Morbid obesity and its concurrent health risks (including diabetes, heart disease and other ailments) are of near-epidemic proportions in industrialized societies. A wide variety of treatments have been proposed and attempted to treat morbid obesity with a wide variety of efficacy and associated morbidity. These treatments include techniques to reduce stomach volume, alter gastric and intestinal motility, and alter the absorption of nutrients in the small intestine.

Clearly, obesity is a complex disease having physiologic, social and psychological components which are not fully understood. The complex nature and the enormous societal implication of obesity require a wide variety of treatment options be available to permit a physician to select a most appropriate option for a particular patient.

Even if all treatments were proven effective, no one treatment can meet the clinical needs presented by a diverse population. For example, bariatric surgeries, such as the Roux-en-Y procedure as will be described, is not considered suitable for only so-called mildly obese patients (e.g., those with a Body Mass Index less than 35).

Less invasive procedures (such as gastric banding) have reduced surgical risk. Unfortunately, they suffer from reduced efficacy (and they are not without risks). Further, efficacy may be culturally biased. Namely, gastric banding studies show reduced efficacy in North American patients compared to European patients.

Surgical approaches may include, e.g., minimally invasive surgery, open surgery and endoscopic approaches to gastric volume reduction. Gastric volume reduction procedures include vertical and horizontal gastroplasty in which sutures, staples or other fixation devices are used to join opposing surfaces of the stomach to create a reduced volume pouch and thereby reduce caloric intake. Less invasive techniques for restricting the volume of the stomach also include a gastric partition in which the stomach wall is endoscopically cinched together to form a reduced size pouch. Other techniques for reducing gastric volume size include placement of obstructions within the stomach.

To address deficiencies associated with gastric volume reduction, treatments have been suggested and developed for reducing the amount of nutrient absorption in the small intestine (particularly in the upper and middle portions of the small intestine—the duodenum and jejunum, respectively). Techniques to reduce nutrient absorption (commonly referred to as malabsorption treatments) include drug therapies for reducing lipids absorption.

Other malabsorption treatments include surgical techniques for rerouting the intestinal system to bypass an extended portion of the small intestine. These include a so-called jejunoileal bypass. Not commonly used due to unacceptable mortality rates, a jejunoileal bypass typically results in effective weight loss. Other techniques include the gastric bypass (or Roux-en Y) and duodenal switch. As a result, the absorptive length of the small intestine is significantly shortened thereby reducing the amount of nutrients which are absorbed into the body and which support or lead to weight gain. These procedures combine the benefits of gastric volume reduction with malabsorption.

Less invasive techniques are suggested for placing a band (referred to as LAP bands) around an upper portion of the stomach to act as a belt to reduce the size of the stomach and create a small passageway (a stoma) from a small upper pouch to the remainder of the stomach.

US Patent Application Publication No. US 2013/0184635 describes a variety of techniques for treating obesity which may include one or more of reducing the rate of stomach emptying, creating a fistula between the stomach and another portion of the gastrointestinal tract two limit nutrient absorption, etc.

US Patent Application Publication No. US 2013/0096580 describes another approach to obesity treatment which involves occluding a blood vessel to interfere with normal gastrointestinal function.

SUMMARY

Methods and apparatus for inducing weight loss using blood flow control are described herein. The apparatus and methods operate by controlling blood flow to the stomach and/or small bowel.

In a first aspect, one or more embodiments of a method of inducing weight loss as described herein may include: making a determination that a patient is ingesting food; and reducing blood flow to the gastrointestinal tract after making the determination that a patient is ingesting food.

In one or more embodiments of methods according to the first aspect, making a determination that a patient is ingesting food comprises one or more of: sensing distention of the patient's stomach, sensing increased pressure in the patient's stomach, sensing swallowing by the patient, receiving direct feedback from the user, and Doppler flow measurements to measure flow velocity.

In one or more embodiments of methods according to the first aspect, reducing blood flow to the gastrointestinal tract comprises mechanically constricting one or more blood vessels that supply the stomach and/or small bowel.

In one or more embodiments of methods according to the first aspect, reducing blood flow to the gastrointestinal tract comprises cooling an exterior surface of one or more blood vessels that supply the stomach and/or small bowel. In one or more embodiments, cooling an exterior surface of one or more blood vessels that supply the stomach and/or small bowel comprises coiling a cooling device around the one or more blood vessels that supply the stomach and/or small bowel.

In one or more embodiments of methods according to the first aspect, reducing blood flow to the gastrointestinal tract comprises cooling blood flowing through one or more blood vessels supplying blood to the stomach and/or the small bowel. In one or more embodiments, the cooling comprises locating a perfusion balloon in a blood vessel and supplying cooling fluid within the perfusion balloon to reduce the temperature of blood flowing through the blood vessel past the perfusion balloon.

In one or more embodiments of methods according to the first aspect, reducing blood flow to the gastrointestinal tract comprises: sensing an increase in blood flow in one or more gastric supply blood vessels; and diverting flow away from the one or more blood vessels that supply the stomach and/or small bowel after sensing the increase in blood flow in the one or more blood vessels that supply the stomach and/or small bowel.

In one or more embodiments of methods according to the first aspect, reducing blood flow to the gastrointestinal tract comprises eluting a drug to reduce flow through one or more blood vessels that supply the stomach and/or small bowel.

In one or more embodiments of methods according to the first aspect, reducing blood flow to the gastrointestinal tract comprises expanding one or more blood vessels that do not that supply the stomach and/or small bowel.

In one or more embodiments of methods according to the first aspect, reducing blood flow to the gastrointestinal tract comprises reducing the flow of blood away from the gastrointestinal tract.

In one or more embodiments of methods according to the first aspect, reducing blood flow to the gastrointestinal tract comprises cooling one or more of: stomach, small bowel, and nerves associated with the stomach and/or small bowel.

In a second aspect, one or more embodiments of a method of inducing weight loss as described herein may include reducing blood flow to the gastrointestinal tract by ablating one or more blood vessels that supply the stomach and/or small bowel to limit dilation of the blood vessels to increase flow after the ablating.

In one or more embodiments of methods according to the second aspect, the ablating is configured to cause fibrosis of the one or more blood vessels that supply the stomach and/or small bowel, wherein the fibrosis limits dilation of the blood vessels to increase flow.

In a third aspect, one or more embodiments of a method of inducing weight loss as described herein may include reducing blood flow to the gastrointestinal tract by ablating one or more nerves selected from the group of: celiac ganglion, superior mesenteric, inferior mesenteric, and hepatic.

In one or more embodiments of methods according to the third aspect, the ablating comprises ablating the one or more nerves using one or more of: direct current electroporation, microwave energy, and radio-frequency energy.

In a fourth aspect, one or more embodiments of a method of inducing weight loss as described herein may include reducing blood flow to the gastrointestinal tract by stimulating one or more peri-arterial nerves to cause vasoconstriction of one or more blood vessels that supply the stomach and/or small bowel.

In a fifth aspect, one or more embodiments of a method of inducing weight loss as described herein may include reducing blood flow to the gastrointestinal tract by pacing one or more peri-arterial nerves to cause vasoconstriction of one or more blood vessels that supply the stomach and/or small bowel.

In a sixth aspect, one or more embodiments of a system for inducing weight loss as described herein may include: a controller operably connected to one or more input devices, wherein the controller is configured to determine that a patient is ingesting food; and one or more blood flow constriction devices operably connected to the controller, the one or more blood flow constriction devices configured to reduce blood flow to the gastrointestinal tract.

In one or more embodiments of systems according to the sixth aspect, the one or more input devices comprise one or more of: a sensor configured to detect distention and/or increased pressure in a stomach, a sensor configured to detect swallowing, and a sensor configured to detect flow into a stomach.

In one or more embodiments of systems according to the sixth aspect, the one or more input devices comprise a direct input device actuated by a patient to provide a signal to the controller that food is being ingested.

In one or more embodiments of systems according to the sixth aspect, the one or more blood flow constriction devices comprises a device configured to mechanically constrict one or more blood vessels that supply the stomach and/or small bowel.

In one or more embodiments of systems according to the sixth aspect, the one or more blood flow constriction devices comprises a device configured to cool an exterior surface of one or more blood vessels that supply the stomach and/or small bowel. In one or more embodiments, the one or more blood flow constriction devices is coiled around the exterior surface of the one or more blood vessels that supply the stomach and/or small bowel.

In one or more embodiments of systems according to the sixth aspect, the one or more blood flow constriction devices comprises a perfusion balloon configured to cool blood flowing through a blood vessel in which the perfusion balloon is located.

As used herein and in the appended claims, the singular forms "a," "an," and "the" include plural referents unless the context clearly dictates otherwise. Thus, for example, reference to "a" or "the" component may include one or more of the components and equivalents thereof known to those skilled in the art. Further, the term "and/or" means one or all of the listed elements or a combination of any two or more of the listed elements.

It is noted that the term "comprises" and variations thereof do not have a limiting meaning where these terms appear in the accompanying description. Moreover, "a," "an," "the," "at least one," and "one or more" are used interchangeably herein.

The above summary is not intended to describe each embodiment or every implementation of the obesity treatment apparatus or methods described herein. Rather, a more complete understanding of the invention will become apparent and appreciated by reference to the following Description of Illustrative Embodiments and claims in view of the accompanying figures of the drawing.

DESCRIPTION OF ILLUSTRATIVE EMBODIMENTS

Figure 1:
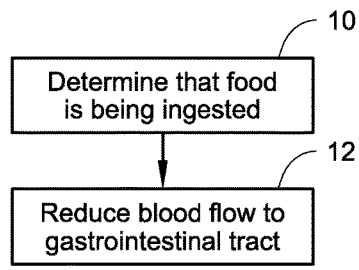
FIG. 1 is a flowchart depicting one illustrative embodiment of a method of inducing weight loss as described herein.

In the following description of illustrative embodiments, reference is made to the accompanying figures of the drawing which form a part hereof, and in which are shown, by way of illustration, specific embodiments. It is to be understood that other embodiments may be utilized and structural changes may be made without departing from the scope of the present invention.

On illustrative embodiment of a method of inducing weight loss is depicted in a flowchart in FIG. 1. In one or more embodiments, the method includes (10) making a determination that a patient is ingesting food, followed by (12) reducing blood flow to the gastrointestinal tract after making the determination that a patient is ingesting food. In other words, control over blood flow to the gastrointestinal tract is based on making a determination that a patient is ingesting food.

That determination, i.e., that a patient is ingesting food can be made by any of a variety of techniques. In one or more embodiments, determining that a patient is ingesting food may be accomplished through a variety of techniques such as, e.g., using a sensor to detect distention of and/or increased pressure in the stomach (using, e.g., pressure sensors, etc.), sensing swallowing by the patient, detecting flow of food into the stomach, detecting changes in luminal fluid (e.g. acidity, bile acid content, fluid volume, solid material), detecting patient activity or movement versus a resting state, detecting gastrointestinal (GI) luminal wall characteristics (e.g. stiffness, thickness), detecting positional changes of recumbency versus standing, etc., and combinations of one or more of these techniques. In one or more alternative embodiments, a patient may provide direct feedback, i.e., an indication that he or she is ingesting food directly as described elsewhere herein. In one or more alternative embodiments, the system can also be selectively and automatically triggered based on time.

Once a determination is made that a patient is ingesting food, one or more embodiments of the methods described herein may include reducing blood flow to one or more portions of the gastrointestinal tract. Reducing blood flow to one or more portions of the gastrointestinal tract may, in one or more embodiments, slow the passage of food through the gastrointestinal tract. Slowing the passage of food out of the stomach may increase the feelings of satiety experienced by the patient which may, in turn, lead to a reduction in food consumption.

In one or more embodiments of the methods described herein, reducing blood flow to the gastrointestinal tract may include mechanically constricting one or more blood vessels that supply the stomach and/or small bowel. Although US Patent Application Publication No. US 2013/0096580 describes obesity treatment methods that involve occluding a blood vessel to interfere with normal gastrointestinal function, those methods are static. In other words, those methods do not include restricting blood flow in response to determining that a patient is ingesting food. The various apparatus and techniques for mechanically constricting blood vessels that supply the stomach and/or small bowel described in that reference may, however, be useful in connection with the methods described herein. Other methods of mechanical constriction may also be used for occluding blood flow, for example, air or fluid filled inflatable cuffs, magnetic devices, a lever- or hinge-based system, vessel retraction toward an anchored structure (e.g. spine), etc.

In one or more embodiments, flow manipulating devices used to reduce blood flow to the gastrointestinal tract may be placed internally or externally in or around a target vessel. These placements could be, e.g., percutaneous, transmural by traversing intestinal wall, via the vasculature or through a laparoscopic or retroperitoneal approach. In one or more embodiments, the flow manipulating devices could include a stimulation system (electrodes, wires, or pneumatic cuff) that, e.g., stimulates nerves that, in turn, constrict the vessel. In one or more embodiments, the flow manipulating devices could include a stimulation system that stimulates the smooth muscle of the vessel and give rise to constriction. In one or more embodiments, the flow manipulating devices may also be utilized in a non-muscular constriction system made up of conformable metals, metalloids, or engineered materials that result in constriction and apposition when electrically stimulated.

Another option for one or more embodiments of a flow manipulating device involves the use of a pneumatic compression device with the air compression chamber involving a diaphragm with one surface exposed to the ring around the vessel of interest and the other to an external compression chamber that could, e.g., be placed subcutaneously or within the abdominal cavity. In one or more embodiments, the pneumatic chamber may involve a system where there is no direct air transport, but rather an electronic system that initiates a biochemical reaction that releases one or more gasses (including, e.g., air) to effect compression or decompression.

In one or more embodiments of the methods described herein, reducing blood flow to the gastrointestinal tract may include cooling an exterior surface of one or more blood vessels that supply the stomach and/or small bowel. Such cooling may, for example, cause the blood vessels to constrict and, thereby, reduce flow. In one or more embodiments, the cooling may be performed by coiling a cooling device around one or more of the blood vessels that supply the stomach and/or small bowel as described in more detail herein. In one or more embodiments of the methods described herein, blood in blood vessels supplying blood to the stomach and/or the small intestine may be selectively directly cooled to restrict flow.

In one or more embodiments, cooling may be used in ways that do not involve direct cooling of blood. In one or more embodiments, the cooling of nerves could result in reflex vasodilation and, in turn, increase the gradient for flow. Cooling also may simply be used to directly suppress appetite by cooling the blood around the stomach and also increase caloric needs and possibly increase metabolic rate as a result of the body needing to increase temperature in response to the cooling.

Figure 2:
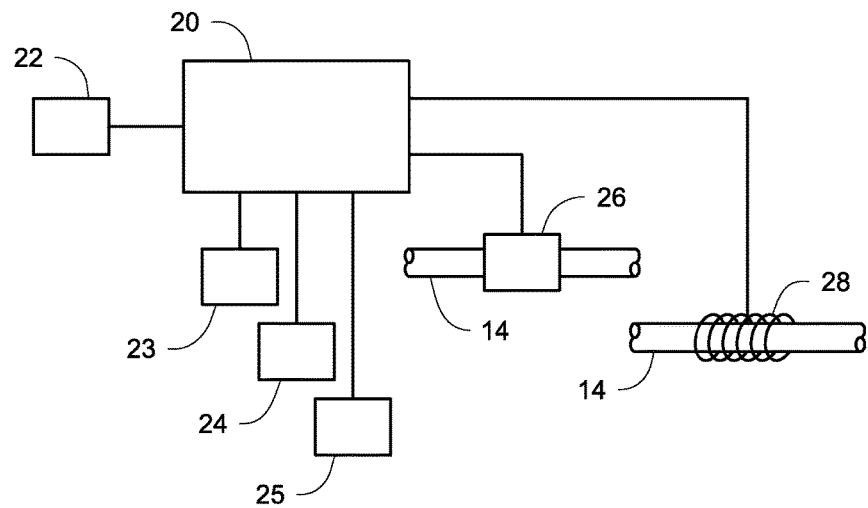
FIG. 2 depicts one illustrative embodiment of an apparatus that may be used to induce weight loss as described herein.

One illustrative embodiment of a system that may be used to induce weight loss in a patient according to one or more of the methods described herein is depicted in FIG. 2. The system includes a controller 20 that is configured to perform the actions described in connection with the methods described herein.

In one or more embodiments, the controller 20 may be connected to an input device 22 that is configured to receive input from a user/patient. The input device 22 may be a wireless input device that communicates wirelessly with the controller 20 which may be implanted subcutaneously within the patient. Some potential embodiments of wireless input devices 22 may include, e.g., smart phones, personal computers, dedicated wireless input devices, etc. In one or more alternative embodiments, the input device 22 may be connected to the controller 20 by wired connection with the input device 22 being in the form of a switch, pushbutton, etc. In those embodiments in which the input device 22 is connected to the controller 20 by wired connection, input device 22 may implanted subcutaneously within the patient.

In one or more embodiments in which the controller 20 is configured to perform a method that includes a determination that a patient is ingesting food, the system may include one or more sensors configured to detect that a patient is ingesting food. In the illustrative embodiment depicted in FIG. 2, the system may include one or more of: a sensor 23 configured to detect distention of and/or pressure increases in the stomach of a patient, a sensor 24 configured to sense swallowing by a patient, and a sensor 25 configured to detect flow of food into the stomach of a patient. Each of the sensors is operably connected to the controller 20 to provide input signals indicative of the ingestion of food by a patient.

The system depicted in FIG. 2 also includes an optional blood vessel constriction device 26 configured to constrict blood flow through a blood vessel 14. The constriction device 26 is operably connected to the controller 20 which is, as described in connection with the methods described herein, configured to operate the constriction device to constrict blood flow through the blood vessel 14.

Another optional device which may be provided in a system such as that depicted in FIG. 2 is a cooling device 28 configured to cool blood flowing through a blood vessel 14 as described in connection with one or more of the methods described herein. The cooling device 28 is operably connected to the controller 20 which is, as described in connection with the methods described herein, configured to operate the cooling device to cool blood flowing through the blood vessel 14. In the depicted illustrative embodiment, the cooling device 28 is in the form of a coiled device coiled around the blood vessel 14, with coolant passing through the coiled device 28 two remove thermal energy from the blood vessel 14 and, therefore, from the blood passing through the blood vessel 14.

Figure 3:
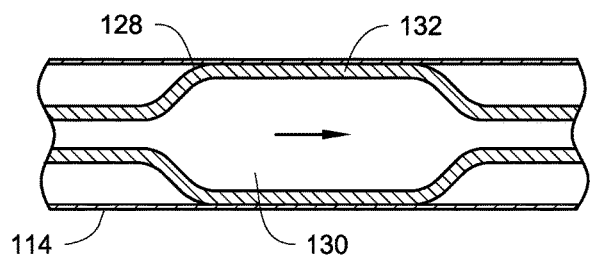
FIG. 3 depicts one illustrative embodiment of an apparatus and method for cooling blood within a blood vessel as described herein.

In one or more embodiments of the methods described herein, the blood flowing through a blood vessel may be cooled as opposed to cooling the exterior surface of the blood vessel. For example, in one or more embodiments, the cooling may be performed by locating a perfusion balloon in a blood vessel and supplying cooling fluid within the perfusion balloon to reduce the temperature of blood flowing through the blood vessel past the perfusion balloon. One illustrative embodiment of a perfusion balloon used to cool blood flowing through a blood vessel is depicted in FIG. 3. In that figure, blood flows through the blood vessel 114 in which a perfusion balloon 128 is located. The direction of blood flow is indicated by the arrow located within the interior 130 of the perfusion balloon 128. The perfusion balloon 128 includes an outer jacket 132 through which a cooling fluid flows to remove thermal energy from the blood flowing through the interior 130 of the perfusion balloon 128. The cooling fluid flowing through jacket 132 may flow in the same direction as the blood flowing through the interior 130 of the perfusion balloon 128 or in the opposite direction. In one or more embodiments, the perfusion balloon 128 may operate to both mechanically constrict flow through the blood vessel 114 as well as cool the blood flowing through that blood vessel.

In one or more embodiments of the methods described herein, reducing blood flow to the gastrointestinal tract may include sensing an increase in blood flow in one or more blood vessels that supply the stomach and/or small bowel; and diverting flow away from the one or more blood vessels after sensing (based on, e.g., dynamic change in vessel size, actual vessel caliber, implantable perivascular ultrasound or laser Doppler, electromagnetic intravascular sensor, etc.) the increase in blood flow in the one or more blood vessels thereby decrease the blood flow to the stomach.

In one or more embodiments of the systems and methods described herein in which Doppler sensing techniques are used to measure velocity of blood flow in a blood vessel, the velocity is related to diameter of the blood vessel. The more a blood vessel is constricted (for a given flow rate), the higher the velocity of blood flowing through that vessel, and the more the blood vessel is dilated, the lower the velocity of blood flowing through the vessel for the same flow rate. Doppler sensing could, in one or more embodiments, be used to make sure that blood flow velocity is set at a certain level. A potential advantage of that approach could include avoiding the need for a separate sensor to detect, e.g., gastric motility, food intake, etc. A potential disadvantage of this approach is that it presupposes that the total amount of blood flow through a blood vessel is constant. However by incorporating vessel diameter measurements, flow rate can be easily calculated. In one or more embodiments of the systems and methods described herein, the Doppler sensor may be advantageously placed in the venous system intravascularly to detect flow either through the vein or from the neighboring artery while an external device could be placed for compression using any of the iterations mentioned herein for the artery. If a sensing device is placed intravascularly, one or more embodiments could be to prepare these sensors with material that prevents blood clotting.

In one or more embodiments of the systems and methods described herein, warming of the surrounding vessels may be needed to increase blood flow other than to the organ of interest, e.g., the stomach. At the same time, cooling may be desired, as described herein, along the artery (or vein—see below) of interest to control blood flow. To achieve these dual purposes and, at the same time, provide for rapid (e.g., near instantaneous) cooling, one or more embodiments of the systems and methods described herein may use the Peltier/Seebeck effects.

Using the Seebeck approach would, e.g., be primarily for generating an electrical signal as feedback when the temperature difference is sufficient between the surrounding tissue (warmer) and the periarterial surface (cooler). This temperature difference using a simple Seebeck generator would, in one or more embodiments, give rise to a signal that would, in turn, shut the device off or reduce the rate of thermal control/regulation. In effect, placement of Seebeck generator in such embodiments could function as a detector of blood flow through a vessel and/or into selected tissue. As the blood flow increased, an electric current (signal) could, in one or more embodiments, be generated as a function of the difference in temperature between the two sides of the element. This temperature change could, therefore, be used in one or more embodiments as an electronic switch or control mechanism as described herein.

The Peltier component of such a system and/or method would, in one or more embodiments, cause the cooling itself using, e.g., a standard battery-capacitor and generator system or simple power supply that might be implanted (potentially inductively charged nocturnally via a charger under the mattress, etc.). One potential disadvantage of thermoelectric generators is that warming occurs on one surface as cooling occurs on another surface (typically on two opposing surfaces). This phenomenon may be used, in one or more embodiments, to advantage by cooling the vessels and/or tissue that are closest to one surface of the device (to, e.g., limit blood flow) and warming vessels and/or tissue the other (e.g., opposite) surface to cause vasodilation. The result may be, in one or more embodiments, reduced blood flow to the stomach and enhanced early satiety. This effect may be amplified if the device is strategically placed, for example, cooling a blood vessel and/or tissue near one surface of the device to limit blood flow, while warming appropriate nerve bundles near the other surface of the device to modulate nerve traffic. Alternatively, the reverse effects could be employed, e.g., the nerve bundles could be cooled to impede conduction, while the blood vessels and/or other tissues are warmed.

In one or more embodiments of the methods described herein, reducing blood flow to the gastrointestinal tract comprises eluting a drug (e.g., vasodilators and/or vasoconstricting agents depending on the particular vessel) to reduce flow through one or more blood vessels that supply the stomach and/or small bowel.

In one or more embodiments, direct electrical stimulation of, e.g., a stent coated with one or more drugs, could give rise to vessel constriction and/or or directly promote satiety could be released on receipt of the electrical impulse (e.g., electrical mediation of drug elution).

In one or more embodiments of the methods described herein, reducing blood flow to the gastrointestinal tract comprises expanding one or more blood vessels that do not supply the stomach and/or small bowel but rather supply other organs, as well as blood vessels (i.e., veins) that drain blood from the GI tract. This diversion will functionally limit the blood flow to the stomach and/or small bowel. One example of such an approach could be timed according to gut distention, where blood goes to the small intestine when food is in the stomach and vice versa. This approach may create a relative deficiency to the area where food needs to be absorbed.

In one or more embodiments of the methods described herein, reducing blood flow to the gastrointestinal tract comprises reducing the flow of blood away from the gastrointestinal tract. It is theorized that reducing the flow of blood away from the gastrointestinal tract may reduce the rate at which blood is delivered to the gastrointestinal tract.

In one or more embodiments of the methods described herein, reducing blood flow to the gastrointestinal tract comprises cooling one or more of: stomach, small bowel, and one or more nerves (e.g., vagus) or ganglia (e.g., celiac) associated with the stomach and/or small bowel. In the methods described thus far, inducing weight loss has been discussed in the context of detecting when a patient is ingesting food and reducing blood flow to one or more portions of the gastrointestinal tract in an effort to induce weight loss. In another approach, one or more embodiments of methods of inducing weight loss may involve reducing blood flow to the gastrointestinal tract by ablating one or more gastric supply blood vessels to limit dilation of the blood vessels to increase flow after the ablating. It is theorized that limiting dilation of the blood vessels will reduce flow that would normally increase after the ingestion of food and during processing of that food within the gastrointestinal tract.

In one or more embodiments of the systems and methods described herein, the autonomic modulation, either through stimulation blockade or ablation may potentially be used alone to control blood flow. In one or more embodiments, a device could be internal/intravascular (vein or artery) or external with, e.g., a cuff-type electrode around the vascular trunks that would include neural bundles which therefore can be stimulated. In such an embodiment, the sensing arm could be a separate sensor that senses one or more of blood flow, gastric motility, glucose, etc. (although in one or more embodiments, the sensor could be incorporated into the effector arm of the device). In other words, the system/method could be configured to monitor neural traffic in a template that is kept normal for that patient during rest, eating, sleep, etc. When a characteristic trigger associated with food ingestion is sensed, stimulation/blockade will be performed and, in turn, have reflex vascular changes that may promote early satiety.

In one or more alternative systems/methods, the functioning may not be based on feedback indicative of the patient eating. In one or more embodiments, for example, the system/method may involve baseline phasic stimulation to increase afferent signaling of satiety, as well as, e.g., increasing vascular tone through the efferent autonomic nerves. The same device could, in one or more embodiments, be used also for direct constriction of the vascular smooth muscle.

In one or more embodiments of systems/methods using ablation, this could be done by a one-time procedure or an implanted device where the ablation is done by the same battery that does the stimulation (DC and DC phasic waveforms). In one or more embodiments, the ablation is not necessarily permanent. It may involve stunning of neurotransmission because of, e.g., reversible electroporation.

In one or more embodiments of inducing weight loss by ablating one or more blood vessels, the ablating (using, e.g., radiofrequency energy, high intensity ultrasound energy, microwave energy, cryothermal energy, transection, photodynamic therapy (PDT), intravascular sclerosant, etc.) is configured to cause fibrosis of the one or more blood vessels that supply the stomach and/or small bowel, wherein the fibrosis limits dilation of the blood vessels to increase flow.

In one or more embodiments of the systems and methods described herein, fibrosis could be facilitated on the vascular wall by ablating either internally or externally. The extent of fibrosis may cause no fixed limitation in terms of blood flow (e.g., stenosis is not necessarily caused), but may limit blood flow by stiffening the vessel wall and limiting the vasodilation and promotional blood flow that occurs as a reflex on, e.g., ingesting food.

In addition to inducing weight loss in methods that involve detecting when a patient is ingesting food and reducing blood flow to one or more portions of the gastrointestinal tract or by ablating one or more blood vessels supplying the gastrointestinal tract, another approach to inducing weight loss as described herein may involve reducing blood flow to the gastrointestinal tract by ablating one or more nerves selected from the group of: celiac ganglion, superior mesenteric, inferior mesenteric, and hepatic.

In one or more embodiments in which one or more nerves are ablated to induce weight loss, the ablation may be performed using one or more of: direct current electroporation, microwave energy, and radio-frequency energy.

In addition to inducing weight loss in methods that involve detecting when a patient is ingesting food and reducing blood flow to one or more portions of the gastrointestinal tract, by ablating one or more blood vessels supplying the gastrointestinal tract, or by ablating one or more nerves as described herein, another approach to inducing weight loss as described herein may involve reducing blood flow to the gastrointestinal tract by stimulating one or more peri-arterial nerves to cause vasoconstriction of one or more gastric supply blood vessels. Yet another potential method for inducing weight loss as described herein may include reducing blood flow to the gastrointestinal tract by pacing one or more peri-arterial nerves to cause vasoconstriction of one or more blood vessels that supply the stomach and/or small bowel.

In one or more embodiments of the systems and methods described herein, stimulation, electroporation, direct radiofrequency energy application, and other thermal approaches, including cooling, of the ganglia (e.g., celiac, mesenteric, hepatic, etc.) could provide indirect effects on satiety by, e.g., changing cellular glucose intake, promoting glycogenolysis, and possibly gluconeogenesis from fat breakdown that may be similar to the effects seen during starvation, exercise, and adrenergic stimulation (via, e.g., the hepatic and related ganglia). These effects may be beneficial and intended/purposeful beyond effects of satiety. In one or more embodiments, improvement of metabolism may indirectly help with obesity, diabetes, possibly hypertension and the metabolic syndrome could potentially be affected through the direct neuroregulatory systems and methods.

In one or more embodiments of the systems and methods described herein, cooling of tissue may be used for the autonomic nerves to produce electroporation without the use of DC current. In one or more embodiments, this effect could result in increased vascular tone at certain locations and decreased vascular tone in others where blood flow is to be promoted. In some instances, there may be combined effects here with cooling directly affecting the vessel, and providing beneficial effects on the perivascular nerves.

Disclosure of any patents, patent documents, and publications identified herein are incorporated by reference in their entirety as if each were individually incorporated. To the extent there is a conflict or discrepancy between this document and the disclosure in any such incorporated document, this document will control.

Illustrative embodiments of the systems and methods are discussed herein some possible variations have been described. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof. It should also be understood that this invention also may be suitably practiced in the absence of any element not specifically disclosed as necessary herein.

What is claimed is:

1. A method of inducing weight loss, the method comprising:
   making a determination that a patient is ingesting food; and
   reducing blood flow to the gastrointestinal tract after making the determination that a patient is ingesting food, wherein reducing blood flow to the gastrointestinal tract comprises cooling an exterior surface of one or more blood vessels that supply the stomach and/or small bowel.

2. A method according to claim 1, wherein making a determination that a patient is ingesting food comprises one or more of: sensing distention of the patient's stomach, sensing increased pressure in the patient's stomach, sensing swallowing by the patient, receiving direct feedback from the user, and Doppler flow measurements to measure flow velocity.

3. A method according to claim 1, wherein reducing blood flow to the gastrointestinal tract comprises mechanically constricting one or more blood vessels that supply the stomach and/or small bowel.

4. A method according to claim 1, wherein cooling an exterior surface of one or more blood vessels that supply the stomach and/or small bowel comprises coiling a cooling device around the one or more blood vessels that supply the stomach and/or small bowel.

5. A method of inducing weight loss, the method comprising:
   making a determination that a patient is ingesting food; and
   reducing blood flow to the gastrointestinal tract after making the determination that a patient is ingesting food, wherein reducing blood flow to the gastrointestinal tract comprises cooling blood flowing through one or more blood vessels supplying blood to the stomach and/or the small bowel.

6. A method according to claim 5, wherein the cooling comprises locating a perfusion balloon in a blood vessel and supplying cooling fluid within the perfusion balloon to reduce the temperature of blood flowing through the blood vessel past the perfusion balloon.

7. A method according to claim 1, wherein reducing blood flow to the gastrointestinal tract comprises:
   sensing an increase in blood flow in one or more gastric supply blood vessels; and
   diverting flow away from the one or more blood vessels that supply the stomach and/or small bowel after sensing the increase in blood flow in the one or more blood vessels that supply the stomach and/or small bowel.

8. A method according to claim 1, wherein reducing blood flow to the gastrointestinal tract comprises eluting a drug to reduce flow through one or more blood vessels that supply the stomach and/or small bowel.

9. A method according to claim 1, wherein reducing blood flow to the gastrointestinal tract comprises expanding one or more blood vessels that do not supply the stomach and/or small bowel.

10. A method according to claim 1, wherein reducing blood flow to the gastrointestinal tract comprises reducing the flow of blood away from the gastrointestinal tract.

11. A method of inducing weight loss, the method comprising:
    making a determination that a patient is ingesting food; and
    reducing blood flow to the gastrointestinal tract after making the determination that a patient is ingesting food, wherein reducing blood flow to the gastrointestinal tract comprises cooling one or more of: stomach, small bowel, and nerves associated with the stomach and/or small bowel.

12. A method according to claim 5, wherein making a determination that a patient is ingesting food comprises one or more of: sensing distention of the patient's stomach, sensing increased pressure in the patient's stomach, sensing swallowing by the patient, receiving direct feedback from the user, and Doppler flow measurements to measure flow velocity.

13. A method according to claim 11, wherein making a determination that a patient is ingesting food comprises one or more of: sensing distention of the patient's stomach, sensing increased pressure in the patient's stomach, sensing swallowing by the patient, receiving direct feedback from the user, and Doppler flow measurements to measure flow velocity.

* * * * *